United States Patent [19]

Balko et al.

[11] 4,153,701

[45] May 8, 1979

[54] 2-SUBSTITUTED-N-(3-SUBSTITUTED PHENYL)-OXAZOLIDINE-3-CARBOTHIOAMIDES

[75] Inventors: Terry W. Balko, Waldron; Ronald E. Hackler, Greenfield, both of Ind.

[73] Assignee: Eli Lilly and Company, Indianapolis, Ind.

[21] Appl. No.: 865,092

[22] Filed: Dec. 27, 1977

[51] Int. Cl.² .................... A61K 31/42; A61K 31/44; C07D 213/90

[52] U.S. Cl. .................................. 424/263; 424/272; 260/307 FA; 546/275; 546/334

[58] Field of Search ................. 260/307 FA, 294.8 E, 260/294.9, 294.8 H; 424/272, 263

[56] References Cited

U.S. PATENT DOCUMENTS 3,546,231  12/1970  King et al. .................... 260/294.8 E Primary Examiner—Jose Tovar
Attorney, Agent, or Firm—Leroy Whitaker; Arthur R. Whale

[57] ABSTRACT

2-Substituted-N-(3-substituted phenyl)oxazolidine-3-carbothioamides, useful as insecticides.

33 Claims, No Drawings

2-SUBSTITUTED-N-(3-SUBSTITUTED PHENYL)-OXAZOLIDINE-3-CARBOTHIOAMIDES

BACKGROUND OF THE INVENTION

This invention relates to oxazolidines. More particularly, this invention relates to 3-substituted-N-(3-substituted phenyl)oxazolidine-3-carbothioamides which are useful as insecticides.

Compounds containing the oxazolidine nucleus are known. For example, German Patent Specification No. 1,445,582 discloses 5-chloromethyl-2-thiocarbamoyliminooxazolidines which are useful as plant growth regulators and anticonvulsants. In addition to 5-chloromethyl-2-thiocarbamoyliminooxazolidines, Belgian Patent No. 643,289 and British Patent Specification No. 1,023,386 disclose 5-methyl-2-thiocarbamoyliminooxazolidines and 5-chloromethyl- and 5-methylthioureido-2-oxazolines, all of which compounds are useful as plant growth regulators and anticonvulsants. U.S. Pat. No. 3,481,950 discloses 5-phenyl-2-thiocarbamoyliminooxazolidin-4-ones which have central nervous system activity. French Pat. No. 2,249,656 discloses 5-methyloxazolidin-2-one-3-carbothioamides having anti-broncho-constricting, anticholinergic, diuretic, analgesic, cardiac analeptic, anticonvulsant, myorelaxant, and anti-inflammatory activity. It may be noted that the generic description of 3-acylaminophenylacetic acid derivatives disclosed in German Patent Specification No. 2,423,536 is sufficiently broad to include N-(3-carboxymethyl)oxazolidine-3-carbothioamides; the disclosed compounds possess pre- and postemergent herbicide activity and plant growth regulant activity. Finally, U.S. Pat. No. 3,546,231 discloses 2-substituted- and 2,2-disubstituted-oxazolidine-3-carbothioamides having nonaryl substitution on the thiocarbamoyl nitrogen; the compounds possess insecticidal and herbicidal activity, especially contact insecticidal activity and pre-emergent herbicidal activity.

SUMMARY OF THE INVENTION

In accordance with the present invention, 2-substituted-N-(3-substituted phenyl)oxazolidine-3-carbothioamides are provided, having the formula,

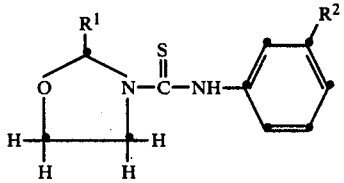

wherein
$R^1$ represents
(A) $C_1-C_6$ alkyl;
(B) $C_3-C_6$ cycloalkyl;
(C) phenyl, optionally monosubstituted with halo; or
(D) 3-pyridyl; and
$R^2$ represents
(A) halo;
(B) trifluoromethyl,
(C) cyano, or
(D) 1,1,2,2-tetrafluoroethoxy.

A preferred group of compounds comprises the compounds of the above formula
in which
$R^1$ represents
(1) $C_5-C_6$ cycloalkyl,
(2) phenyl, optionally monosubstituted with halo, or
(3) 3-pyridyl; and
$R^2$ represents halo.

A more preferred group of compounds comprises the compounds of the above formula
in which
$R^1$ represents
(1) cyclohexyl,
(2) phenyl,
(3) 2-chlorophenyl,
(4) 4-bromophenyl, or
(5) 3-pyridyl; and
$R^2$ represents chloro or bromo.

The present invention also provides a method for reducing or eradicating a population of the insect species *Epilachna varivestis* which comprises administering to the insect by ingestion an insecticidally-effective amount of a compound of the above formula.

Additionally, the present invention provides an insecticidal composition which comprises an insecticidally-effective amount of a compound of the above formula and an agriculturally-acceptable carrier.

DETAILED DESCRIPTION OF THE INVENTION

In the above formula, the various chemical groups have their usual meanings. For the sake of clarity, however, examples of the various generally-named groups will be given.

The term "$C_1-C_6$ alkyl" includes methyl, ethyl, propyl, isopropyl, butyl, isobutyl, sec-butyl, t-butyl, pentyl, isopentyl, 1-methylbutyl, 1-ethylpropyl, neopentyl, hexyl, isohexyl, and the like. The term "$C_3-C_6$ cycloalkyl" includes cyclopropyl, cyclobutyl, cyclopentyl, cyclohexyl, and the like. Similarly, the phrase "phenyl, optionally monosubstituted with . . ." is meant to include, among others, such groups as phenyl, 2-fluorophenyl, 3-chlorophenyl, 4-bromophenyl, 3-iodophenyl, and the like.

It will be understood that the present invention is not to be limited by the definitions and exemplification given herein. Various classes of compounds are contemplated, and such various classes of compounds can be employed in either the method or the insecticidal composition of the present invention. Examples of such contemplated various classes are given below. Each numbered subparagraph describes an independent class of compounds; in each class, the variables have the general meanings already given if not otherwise stated.
Compounds wherein:
1. $R^1$ represents $C_1-C_6$ alkyl;
2. $R^1$ represents $C_3-C_6$ cycloalkyl;
3. $R^1$ represents phenyl or substituted phenyl;
4. $R^1$ represents 3-pyridyl;
5. $R^1$ represents $C_5-C_6$ cycloalkyl;
6. $R^1$ represents cyclohexyl;
7. $R^1$ represents phenyl;
8. $R^1$ represents 2-chlorophenyl or 4-bromophenyl;
9. $R^2$ represents halo, trifluoromethyl, cyano, or 1,1,2,2-tetrafluoroethoxy;
10. $R^2$ represents halo;
11. $R^2$ represents chloro or bromo;
12. The variables are as described in subparagraphs 2 and 9;
13. The variables are as described in subparagraphs 2 and 10;

14. The variables are as described in subparagraphs 2 and 11;
15. The variables are as described in subparagraphs 3 and 9;
16. The variables are as described in subparagraphs 3 and 10;
17. The variables are as described in subparagraphs 3 and 11;
18. The variables are as described in subparagraphs 4 and 9;
19. The variables are as described in subparagraphs 4 and 10;
20. The variables are as described in subparagraphs 4 and 11;
21. The variables are as described in subparagraphs 5 and 9;
22. The variables are as described in subparagraphs 5 and 10;
23. The variables are as described in subparagraphs 5 and 11;
24. The variables are as described in subparagraphs 6 and 9;
25. The variables are as described in subparagraphs 6 and 10;
26. The variables are as described in subparagraphs 6 and 11;
27. The variables are as described in subparagraphs 7 and 9;
28. The variables are as described in subparagraphs 7 and 10;
29. The variables are as described in subparagraphs 7 and 11;
30. The variables are as described in subparagraphs 8 and 9;
31. The variables are as described in subparagraphs 8 and 10; and
32. The variables are as described in subparagraphs 8 and 11.

It should be apparent from the foregoing that any and all possible combinations of variables are within the scope of the present invention. From the above examples of contemplated classes, it is possible for one having ordinary skill in the art to construct any desired class, whether specifically exemplified or not. Thus, the present invention consists of multiple subgenera, with each subgenus consisting of a contemplated class of compounds as illustrated above without being limited thereto. Stated differently, any subgenus not specifically set forth herein is still implicitly within the scope of the present invention.

In order to further clarify the present invention, the following list of compounds is given by way of illustration. It is to be understood, however, that the present invention is neither confined to nor limited by the compounds listed.

1. N-(3-bromophenyl)-2-methyloxazolidine-3-carbothioamide,
2. 2-ethyl-N-(3-trifluoromethylphenyl)oxazolidine-3-carbothioamide,
3. N-(3-iodophenyl)-2-propyloxazolidine-3-carbothioamide,
4. N-(3-fluorophenyl)-2-isopropyloxazolidine-3-carbothioamide,
5. 2-butyl-N-(3-cyanophenyl)oxazolidine-3-carbothioamide,
6. 2-sec-butyl-N-[3-(1,1,2,2-tetrafluoroethoxy)phenyl]oxazolidine-3-carbothioamide,
7. N-(3-chlorophenyl)-2-isobutyloxazolidine-3-carbothioamide,
8. 2-t-butyl-N-(3-fluorophenyl)oxazolidine-3-carbothioamide,
9. N-(3-iodophenyl)-2-pentyloxazolidine-3-carbothioamide,
10. 2-(1-methylbutyl)-N-(3-trifluoromethylphenyl)oxazolidine-3-carbothioamide,
11. N-(3-cyanophenyl)-2-(1-ethylpropyl)oxazolidine-3-carbothioamide,
12. N-(3-fluorophenyl)-2-neopentyloxazolidine-3-carbothioamide,
13. 2-t-pentyl-N-[3-(1,1,2,2-tetrafluoroethoxy)phenyl]oxazolidine-3-carbothioamide,
14. N-(3-chlorophenyl)-2-hexyloxazolidine-3-carbothioamide,
15. 2-(2,3-dimethylbutyl)-N-(3-iodophenyl)oxazolidine-3-carbothioamide,
16. 2-cyclopropyl-N-(3-fluorophenyl)oxazolidine-3-carbothioamide,
17. 2-cyclobutyl-N-(3-trifluoromethylphenyl)oxazolidine-3-carbothioamide,
18. N-(3-cyanophenyl)-2-cyclopentyloxazolidine-3-carbothioamide,
19. N-(3-bromophenyl)-2-cyclohexyloxazolidine-3-carbothioamide,
20. N-(3-iodophenyl)-2-phenyloxazolidine-3-carbothioamide,
21. N-(3-fluorophenyl)-2-(2-fluorophenyl)oxazolidine-3-carbothioamide,
22. 2-(3-bromophenyl)-N-(3-chlorophenyl)oxazolidine-3-carbothioamide,
23. 2-(3-iodophenyl)-N-(3-trifluoromethylphenyl)oxazolidine-3-carbothioamide, and
24. N-(3-cyanophenyl)-2-(3-pyridyl)oxazolidine-3-carbothioamide.

The compounds of the present invention are prepared in accordance with methods well known to those having ordinary skill in the art. In general, the compounds can be prepared by reacting an appropriately-substituted 2-methyleneaminoethanol with an equivalent amount of a suitably-substituted phenyl isothiocyanate, as shown by the following equation:

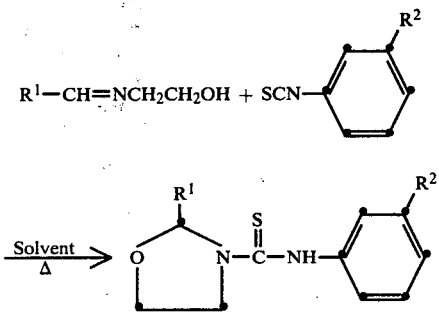

The reaction usually is carried out in a suitable solvent at an elevated temperature, usually at the reflux temperature of the reaction mixture. Suitable solvents include, among others, benzene, toluene, the xylenes, chloroform, ethyl acetate, acetonitrile, diethyl ether, and the like. The preferred solvents are toluene, diethyl ether, and chloroform. The reaction mixture then is worked up in accordance with usual procedures. Typically, the solvent is removed under reduced pressure and the residue recrystallized from a suitable solvent or solvent combination. The most frequently used recrystallization solvents and solvent combinations are benzene, ethanol, aqueous ethanol, carbon tetrachloride/hexane, and cyclohexane/diethyl ether.

The 2-methyleneaminoethanol is a Schiff base that is in equilibrium with the corresponding oxazolidine having only the $R^1$ substituent; see E. D. Bergmann, Chem. Rev., 53, 309 (1953). As the oxazolidine in the equilibrium mixture reacts with the isothiocyanate, the equilibrium shifts, allowing the reaction to go to completion.

The 2-methyleneaminoethanol starting materials in general are prepared, in accordance with known procedures, by reacting the appropriately-substituted aldehyde with 2-aminoethanol. Typically, the reaction is carried out in benzene or toluene and the resulting water of condensation is removed by azeotropic distillation and collected in a Dean-Stark trap. While catalysts do not appear to be necessary, the reaction can be carried out in the presence of a catalytic amount of hydrogen chloride, typically added as concentrated hydrochloric acid.

The phenyl isothiocyanate starting materials also are readily prepared by known methods from the corresponding anilines. For example, the appropriately-substituted aniline is reacted with N,N-dimethylthiocarbamoyl chloride in a suitable solvent, such as benzene, toluene, or a xylene. Typically, the reaction is carried out at reflux temperature for approximately 14 hours. The resulting phenyl isothiocyanate normally is isolated and purified by distillation. Alternatively, the appropriately-substituted aniline can be reacted with thiophosgene in chloroform in the presence of aqueous sodium carbonate at a temperature of 10°-15° C.

With respect to the required aldehydes and anilines, such compounds are either available commercially or readily prepared by known methods. For an excellent summary of typical preparative methods, see R. B. Wagner and H. D. Zook, "Synthetic Organic Chemistry," John Wiley and Sons, Inc., New York, 1953.

The examples which follow illustrate the preparations of representative compounds of the present invention. The first example illustrates the preparation of a 2-methyleneaminoethanol. In most cases the product was identified by elemental microanalysis and nuclear magnetic resonance analysis. Unless otherwise stated, all temperatures are given in degrees Celsius.

EXAMPLE 1

Preparation of 2-[(4-bromophenylmethylene)amino]ethanol

A mixture of 18.5 g. of p-bromobenzaldehyde, 6.1 g. of 2-aminoethanol, about 100 ml. of toluene, and 0.5 ml. of concentrated hydrochloric acid was heated at reflux for about 14 hours; the water of condensation was removed by azeotropic distillation and collected in a Dean-Stark trap. The reaction mixture then was cooled and the solvent was distilled under reduced pressure. The residue was recrystallized from benzene/hexane to give 18.1 g. (79%) of 2-[(4-bromophenylmethylene)amino]ethanol, m.p. 79°-81° C. The following elemental microanalysis was obtained:

Calculated for $C_9H_{10}BrNO$: C, 47.39; H, 4.42; N, 6.14. Found: C, 47.10; H, 4.25; N, 6.05.

EXAMPLE 2

Preparation of N-(3-Chlorophenyl)-2-cyclohexyl-oxazolidine-3-carbothioamide

A mixture of 1.6 g. of 2-[(cyclohexylmethylene)amino]ethanol, 1.7 g. of 3-chlorophenyl isothiocyanate, and about 100 ml. of diethyl ether was heated at reflux for about 108 hours. The solvent was distilled under reduced pressure. The residue was recrystallized from cyclohexane/diethyl ether to give 1.2 g. (37%) of N-(3-chlorophenyl)-2-cyclohexyloxazolidine-3-carbothioamide, m.p. 117°-9° C. The following elemental microanalysis was obtained:

Calculated for $C_{16}H_{21}ClN_2OS$: C, 59.15; H, 6.32; N, 8.62. Found: C, 59.04; H, 6.36; N, 8.73.

The following compounds were prepared by the general procedure of Example 2. In each case, the reaction time and reaction solvent are given. When available, the percent yield, melting point, recrystallization solvent, and elemental microanalysis also are given.

EXAMPLE 3

N-(3-Chlorophenyl)-2-phenyloxazolidine-3-carbothioamide 16 hours, chloroform, 23%, 99°-102° C., carbon tetrachloride/hexane.

Calculated for $C_{16}H_{15}ClN_2OS$: C, 60.28; H, 4.71; N, 8.79. Found: C, 59.51; H, 4.64; N, 8.54.

Nuclear magnetic resonance analysis was high in the aromatic region. Mass spectrographic analysis gave a peak of 318.

EXAMPLE 4

2-(2-Chlorophenyl)-N-(3-chlorophenyl)oxazolidine-3-carbothioamide 16 hours, diethyl ether, 59%, 140°-1° C.

Calculated for $C_{16}H_{14}Cl_2N_2OS$: C, 54.40; H, 3.99; N, 7.93. Found: C, 54.21; H, 3.82; N, 7.96.

EXAMPLE 5

2-(4-Bromophenyl)-N-(3-chlorophenyl)oxazolidine-3-carbothioamide 16 hours, toluene, 61%, 127°-9° C., aqueous ethanol.

Calculated for $C_{16}H_{14}BrClN_2OS$: C, 48.32; H, 3.54; N, 7.04. Found: C, 48.34; H, 3.72; N, 7.08.

EXAMPLE 6

N-(3-Bromophenyl)-2-(4-bromophenyl)oxazolidine-3-carbothioamide 16 hours, toluene, 132°-3° C., ethanol.

Calculated for $C_{16}H_{14}Br_2N_2OS$: C, 43.46; H, 3.19; N, 6.34. Found: C, 43.70; H, 3.31; N, 6.36.

EXAMPLE 7

N-(3-Chlorophenyl)-2-(3-pyridyl)oxazolidine-3-carbothioamide 16 hours, diethyl ether, 80%, 141°-4° C.

Calculated for $C_{15}H_{14}ClN_3OS$: C, 56.33; H, 4.41; N, 13.14. Found: C, 56.08; H, 4.21; N, 13.25.

The compounds of the present invention are useful for the control of insect pests. For example, the compounds are active against such insects as Mexican bean beetle, boll weevil, corn rootworm, cereal leaf beetle, flea beetle, borers, Colorado potato beetle, grain beetles, alfalfa weevil, carpet beetle, confused flour beetle, powder post beetle, wireworms, rice weevil, rose beetle, plum curculio, white grubs, melon aphid, rose aphid, white fly, grain aphid, corn leaf aphid, rose aphid, white fly, grain aphid, corn leaf aphid, pea aphid, mealy-bugs, scales, leafhopper, citrus aphid, spotted alfalfa aphid, green peach aphid, bean aphid, milkweed bug, chinch bug, housefly, yellow-fever mosquito, stable fly, horn fly, cabbage maggot, carrot rust fly, codling moth, cutworm, clothes moth, Indian meal moth, leafrollers, corn earworm, European corn borer, cabbage looper, cotton bollworm, bagworm, sod webworm, fall armyworm, German cockroach, and American cockroach.

Because the compounds of the present invention appear to function most effectively when ingested by the target insect, such compounds are particularly useful for the control of insect pests on plants, and especially for the control of Mexican bean beetles. In general, however, the compounds of the present invention can be applied to or incorporated into any food or water source for the target insect.

Thus, the present invention provides a method for reducing or eradicating a population of the insect species *Epilachna varivestis* which comprises administering to the insect by ingestion an insecticidally-effective amount of a compound of the present invention.

The term "insecticidally-effective amount" refers to an amount which results in the inactivation of the insect. Such inactivation can be lethal, either immediately or with delay, or it can be a sub-lethal inactivation in which the insect is rendered incapable of carrying out one or more of its normal life processes. Thus, the term "reducing or eradicating" means that the compound of the present invention can either kill all of the insect species to which the compound is administered, or that the administration of the compound reduces the population of such insect species. As is well known in the art, many known insecticides render the insect incapable of carrying out one or more of its normal life processes. Most often, the nervous system typically is seriously disturbed. However, the precise mechanism by which the compounds constituting the present invention operate is not yet known, and the insecticidal methods of the present invention are not limited by any mode of operation.

The utilization of an inactivating amount of one of the compounds of the present invention is critical to the insecticidal method of the present invention. The inactivating amount can sometimes be administered by employing the compound in unmodified form. However, for best results, it generally is necessary that the compound or compounds be employed in modified form; that is, as one component of a composition formulated to implement the insecticidal effects. Thus, for example, the active ingredient can be mixed with water or other liquid or liquids, preferably aided by the usage of a surface-active agent. The compounds also can be incorporated on finely-divided solid, which can be a substance having surface-active adsorption properties, to yield a wettable powder which subsequently can be dispersed in water or other liquid, or incorporated as part of a dust which can be applied directly. Other methods of formulation are known in the art and can be employed in implementing the present invention.

The exact concentration of one or more of the compounds of the present invention in a composition thereof with one or a plurality of adjuvants can vary; it is necessary only that one or more of the products be present in such amount as to make possible the application of an inactivating dosage to an insect. In many situations, a composition comprising about 0.001 percent by weight of the present active agent is effective for the administration of an inactivating amount thereof to insect pests. Compositions having a higher concentration of active agent, such as a concentration of from about 0.001 to about 0.5 percent can, of course, be employed. In still other operations, compositions containing from about 0.5 to about 98 percent by weight of one or more compounds are conveniently employed. Such compositions are adapted to be employed as treating compositions per se or as concentrates for subsequent dilution with additional adjuvant to produce ultimate treating compositions.

Liquid compositions containing the desired amount of active agent are prepared by dissolving the substance in an organic liquid or by dispersing the substance in water with or without the aid of a suitable surface-active dispersing agent such as an ionic or nonionic emulsifing agent. Such compositions also can contain modifying substances which serve to aid spreading and adhesion of the material on plant foliage. Suitable organic liquid carriers include the agricultural spray oils and the petroleum distillates such as diesel fuel, kerosine, fuel oil, naphthas, and Stoddard solvent. Among such liquids the petroleum distillates are generally preferred. The aqueous compositions can contain one or more water-immiscible solvents for the toxicant compound. In such aqueous compositions, the carrier comprises an aqueous emulsion, e.g., a mixture of water, emulsifying agent, and water-immiscible solvent. The choice of dispersing and emulsifying agent and the amount thereof employed is dictated by the nature of the composition and by the ability of the agent to facilitate the dispersing of the active agent in the carrier to produce the desired composition. Dispersing and emulsifying agents which can be employed in the compositions include the condensation products of alkylene oxides with phenols and organic acids, alkaryl sulfonates, polyoxyalkylene derivatives of sorbitan esters, complex ether alcohols, and the like. For a review of known surface-active agents which are suitably employed in implementing the present invention, attention is directed to U.S. Pat. No. 3,095,299, second column, lines 25-36, and references cited therein.

In the preparation of dust compositions, the active ingredient is intimately dispersed in and on a finely-divided solid such as clay, talc, chalk, gypsum, lime stone, vermiculite fines, perlite, and the like. In one method of achieving such dispersion, the finely divided carrier is mechanically mixed or ground with the active agent.

Similarly, dust compositions containing the toxicant compounds can be prepared with various of solid carriers such as bentonite, fuller's earth, attapulgite, and other clays having surface-active adsorption properties. Depending upon the proportions of ingredients, these dust compositions can be employed as concentrates and subsequently diluted with additional adsorptive-type solid carriers or with chalk, talc, or gypsum, or the like to obtain the desired amount of active ingredient in a composition adapted to be employed in accordance with the present invention. Also, such dust compositions can be dispersed in water, with or without the aid of a dispersing agent, to form spray mixtures.

The compositions of the present invention also can be employed in granular formulations. These formulations are prepared in conventional manner, typically by dissolving the compound in a solvent with or without a surface-active agent and spraying or otherwise distributing the resulting solution onto pre-formed granules. Such granular formulations are capable of providing longer-lasting activity and may be preferred for crops such as corn where repeated application is not practical.

When operating in accordance with the present invention, one or more of the compounds or a composition containing one or more of the compounds is applied to a source of food or water for the pest to be controlled in any convenient manner, for example, by means of hand dusters or sprayers or by simple mixing with the food to be ingested by the pests. Application to the foliage of plants is conveniently carried out with power dusters, boom sprayers, and fog sprayers. In such foliar applications, the employed composition should not contain any appreciable amounts of any phytotoxic diluents. In large-scale operations, dust or low volume sprays can be applied from the air. The present invention also comprehends the employment of compositions comprising one or more of compounds of the present invention, an adjuvant, and one or more other biologically-active materials, such as other insecticides, fungicides, miticides, bacteriocides, nematocides, and the like.

It is usual in describing foliar applications of plant protectants to measure the application rate by the concentration of dispersion in which it is applied. The application rate is measured in this way because it is customary to apply a sufficient amount of the dispersion to cover the foliage with a thin film. The amount of dispersion applied is thus dependent on the foliar area of the plant, and the quantity of plant-protecting compound is dependent upon its concentration in the dispersion.

Thus, in one embodiment, the insecticidal method is carried out by applying the compounds to the foliage of plants or other source of food for the insect, and applications are made in the same manner as already described. The insecticidal application rates are from about 10 ppm to about 2000 ppm. It is, of course, apparent that higher or lower concentrations can be employed, depending upon the insect species to be controlled, the plant or other food source to which application is to be made, and the potency or toxicity of the particular compound in the composition.

The activity of representative compounds of the present invention against Mexican bean beetle is illustrated by the following example.

EXAMPLE 8

The compounds to be tested were dissolved or suspended in 50:50 acetone:ethanol, and a blend of anionic and nonionic surfactants was added. The solution then was dispersed in water, so that the final dispersion contained about 20 percent of solvent and the concentration of test compound shown in the table below.

The test compound dispersions were sprayed on the foliage of young bean plants in an amount sufficient to wet the foliage completely. The dispersions then were allowed to dry, and individual leaves were removed from the plants. The petiole of each leaf was wrapped in water-soaked cotton and the leaf then was infested with second instar larva of Mexican bean beetle. Five larva were applied to each leaf, and two replicates were used for each compound concentration. Mortality was observed on the fourth and seventh days after treatment.

Untreated control insects were included with every group of test insects.

Insect mortality produced by the compound was rated on a scale where 0 represented no mortality, 1 represented less than 50 percent mortality, 2 represented 51–99 percent mortality, and 3 represented 100 percent mortality of insects. Results were averaged where a compound was tested repeatedly against the insect. Empty spaces in the table indicate that the compound was not tested at the indicated rate. The results produced by typical compounds of the invention are summarized in Table 1 which follows.

TABLE 1

| | ACTIVITY OF REPRESENTATIVE COMPOUNDS AGAINST MEXICAN BEAN BEETLE | | | | | | | | |
|---|---|---|---|---|---|---|---|---|---|
| | ORIGINAL TEST | | | | RETEST | | | | |
| Compound of Example | 1000 ppm. 4 days | 7 days | 100 ppm. 4 days | 7 days | 100 ppm. 7 days | 50 ppm. 7 days | 25 ppm. 7 days | 10 ppm. 7 days | 5 ppm. 7 days |
| 2 | 3 | | 0 | | | | | | |
| 3 | | | | | 3 | 2 | 1 | 1 | |
| 4 | 3 | 3 | | | | | | | |
| 5 | 3 | 3 | 0 | 1 | | | | | |
| 6 | 3 | 3 | 1 | 1 | | | | | |
| 7 | 3 | 3 | | | | | | | |

What is claimed is:

1. A compound of the formula,

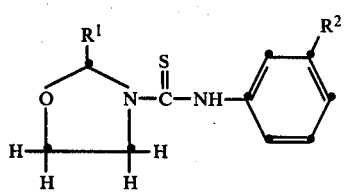

wherein
R[1] represents
(A) $C_1$–$C_6$ alkyl;
(B) $C_3$–$C_6$ cycloalkyl;
(C) phenyl, optionally monosubstituted with halo; or
(D) 3-pyridyl; and
R[2] represents
(A) halo,
(B) trifluoromethyl,
(C) cyano, or
(D) 1,1,2,2-tetrafluoroethoxy.

2. A compound of claim 1, wherein R[1] represents $C_5$–$C_6$ cycloalkyl; phenyl, optionally monosubstituted with halo; or 3-pyridyl.

3. A compound of claim 1, wherein R[1] represents cyclohexyl, phenyl, 2-chlorophenyl, 4-bromophenyl, or 3-pyridyl.

4. A compound of claim 1, wherein $R^2$ represents halo.

5. A compound of claim 1, wherein $R^2$ represents chloro or bromo.

6. The compound of claim 1, which compound is N-(3-chlorophenyl)-2-cyclohexyloxazolidine-3-carbothioamide.

7. The compound of claim 1, which compound is N-(3-chlorophenyl)-2-phenyloxazolidine-3-carbothioamide.

8. The compound of claim 1, which compound is 2-(2-chlorophenyl)-N-(3-chlorophenyl)oxazolidine-3-carbothioamide.

9. The compound of claim 1, which compound is 2-(4-bromophenyl)-N-(3-chlorophenyl)oxazolidine-3-carbothioamide.

10. The compound of claim 1, which compound is N-(3-bromophenyl)-2-(4-bromophenyl)oxazolidine-3-carbothioamide.

11. The compound of claim 1, which compound is N-(3-chlorophenyl)-2-(3-pyridyl)oxazolidine-3-carbothioamide.

12. A method for reducing or eradicating a population of the insect species *Epilachna varivestis* which comprises administering to the insect by ingestion an insecticidally-effective amount of a compound of claim 1.

13. A method of claim 12, wherein $R^1$ represents $C_5$–$C_6$ cycloalkyl; phenyl, optionally monosubstituted with halo; or 3-pyridyl.

14. A method of claim 12, wherein $R^1$ represents cyclohexyl, phenyl, 2-chlorophenyl, 4-bromophenyl, or 3-pyridyl.

15. A method of claim 12, wherein $R^2$ represents halo.

16. A method of claim 12, wherein $R^2$ represents chloro or bromo.

17. The method of claim 12, in which the compound is N-(3-chlorophenyl)-2-cyclohexyloxazolidine-3-carbothioamide.

18. The method of claim 12, in which the compound is N-(3-chlorophenyl)-2-phenyloxazolidine-3-carbothioamide.

19. The method of claim 12, in which the compound is 2-(2-chlorophenyl)-N-(3-chlorophenyl)oxazolidine-3-carbothioamide.

20. The method of claim 12, in which the compound is 2-(4-bromophenyl)-N-(3-chlorophenyl)oxazolidine-3-carbothioamide.

21. The method of claim 12, in which the compound is N-(3-bromophenyl)-2-(4-bromophenyl)oxazolidine-3-carbothioamide.

22. The method of claim 12, in which the compound is N-(3-chlorophenyl)-2-(3-pyridyl)oxazolidine-3-carbothioamide.

23. An insecticidal composition which comprises an insecticidally-effective amount of a compound of claim 1 and an agriculturally-acceptable carrier.

24. A composition of claim 23, wherein $R^1$ represents $C_5$–$C_6$ cycloalkyl; phenyl, optionally monosubstituted with halo; or 3-pyridyl.

25. A composition of claim 23, wherein $R^1$ represents cyclohexyl, phenyl, 2-chlorophenyl, 4-bromophenyl, or 3-pyridyl.

26. A composition of claim 23, wherein $R^2$ represents halo.

27. A composition of claim 23, wherein $R^2$ represents chloro or bromo.

28. The composition of claim 23, in which the compound is N-(3-chlorophenyl)-2-cyclohexyloxazolidine-3-carbothioamide.

29. The composition of claim 23, in which the compound is N-(3-chlorophenyl)-2-phenyloxazolidine-3-carbothioamide.

30. The composition of claim 23, in which the compound is 2-(2-chlorophenyl)-N-(3-chlorophenyl)oxazolidine-3-carbothioamide.

31. The composition of claim 23, in which the compound is 2-(4-bromophenyl)-N-(3-chlorophenyl)oxazolidine-3-carbothioamide.

32. The composition of claim 23, in which the compound is N-(3-bromophenyl)-2-(4-bromophenyl)oxazolidine-3-carbothioamide.

33. The composition of claim 23, in which the compound is N-(3-chlorophenyl)-2-(3-pyridyl)oxazolidine-3-carbothioamide.

* * * * *